(12) United States Patent
Gupta et al.

(10) Patent No.: US 6,789,410 B1
(45) Date of Patent: Sep. 14, 2004

(54) METHOD AND APPARATUS FOR REDUCTION OF GAS BUBBLE FORMATION DUE TO GAS DIFFUSION THROUGH LIQUIDS CONTAINED IN PORES

(76) Inventors: Krishna M. Gupta, 12 Grandview Dr., Ithaca, NY (US) 14850; Valeriu Smiricinschi, 316 Highland Rd. Apt B204, Ithaca, NY (US) 14850

( * ) Notice: Subject to any disclaimer, the term of this patent is extended or adjusted under 35 U.S.C. 154(b) by 0 days.

(21) Appl. No.: 10/651,074

(22) Filed: Aug. 28, 2003
(Under 37 CFR 1.47)

(51) Int. Cl.[7] ............................................... G01N 15/08
(52) U.S. Cl. ...................................................... 73/38
(58) Field of Search ........................................... 73/38

(56) References Cited

U.S. PATENT DOCUMENTS

| | | | |
|---|---|---|---|
| 2,465,948 A | | 3/1949 | Welge ............................. 73/38 |
| 2,534,737 A | | 12/1950 | Rose .............................. 73/38 |
| 2,612,036 A | | 9/1952 | Angona ........................... 73/38 |
| 2,706,904 A | | 4/1955 | Hertel ............................. 73/38 |
| 2,755,660 A | | 7/1956 | Kammermeyer et al. ....... 73/38 |
| 4,203,317 A | | 5/1980 | Gupta ............................. 73/38 |
| 4,217,336 A | | 8/1980 | Maire et al. ................. 423/448 |
| 4,576,927 A | | 3/1986 | Kuroda et al. .............. 502/402 |
| 4,660,412 A | | 4/1987 | Gupta ............................. 73/38 |
| 4,744,240 A | | 5/1988 | Reichelt ......................... 73/38 |
| 5,151,187 A | * | 9/1992 | Behmann .................... 210/607 |
| 5,316,682 A | * | 5/1994 | Keyser et al. .............. 210/649 |
| 5,674,404 A | * | 10/1997 | Kenley et al. .............. 210/741 |
| 5,695,818 A | | 12/1997 | Soffer et al. ............. 427/248.1 |
| 5,696,198 A | | 12/1997 | Chereisky et al. .......... 524/496 |
| 5,955,185 A | | 9/1999 | Yoshino et al. .......... 428/304.4 |

FOREIGN PATENT DOCUMENTS

| | | | |
|---|---|---|---|
| DE | 1927171 | 12/1970 | .......... G01N/13/04 |
| DE | 3312729 A1 | 10/1984 | .......... G01N/15/08 |
| DE | 19858338 | 12/1997 | .......... G01N/15/08 |
| EP | 0139202 | 5/1985 | .......... G01N/15/08 |
| EP | 0831318 | 3/1998 | .......... G01N/15/08 |
| RU | 229002 | 2/1969 | ..................... 73/38 |
| RU | 853492 | 8/1981 | ..................... 73/38 |
| RU | 1118900 | 10/1984 | ..................... 73/38 |
| RU | 1130772 | 12/1984 | ..................... 73/38 |
| RU | 1807341 | 4/1993 | ..................... 73/38 |

OTHER PUBLICATIONS

Jena, Akshaya K. and Gupta, Krishna M.. "In–Plane Compression Porometry of Battery Separators." Journal of Power Sources 80. 1999. p. 46–52.

Gupta, Vibhor and Jena, A.K.. "Substitution of Alcohol in Porometers For Bubble Point Determination." Advances in Filtration and Separation Technology. Col. 13b, 1999 p. 833–844.

(List continued on next page.)

*Primary Examiner*—Hezron Williams
*Assistant Examiner*—John Fitzgerald
(74) *Attorney, Agent, or Firm*—Brown & Michaels, PC

(57) ABSTRACT

A porosimeter includes a pressurizable sample chamber with a membrane located directly below the sample. The membrane pores have a smaller size than any of the sample pores of interest. A fluid reservoir is located below the membrane such that the reservoir and the membrane form a seal. In operation, as fluid enters the fluid reservoir through the membrane or a reservoir inlet, fluid already in the fluid reservoir is displaced through a reservoir exit. An inlet in a fluid displacement reservoir receives the fluid displaced from the fluid reservoir. A recirculation line receives fluid from the exit of the fluid displacement reservoir and circulates the fluid into the inlet of the fluid reservoir. In a preferred embodiment, a pump recirculates the fluid through the recirculation line. Fluid returned to the reservoir circulates over the bottom of the membrane, and sweeps air bubbles out of the reservoir.

25 Claims, 3 Drawing Sheets

OTHER PUBLICATIONS

Gupta, Nalini and Jena, Akshaya. "Measuring in Layers: Determining the Pore Structure of Individual Layers of Multi–Layered Ceramic Composites." Ceramic Industry, Feb. 2001, p. 28–33.

Jena, Akshaya K. and Gupta, Krishna M. "Determination of Pore Volume and Pore Distribution by Liquid Extrusion Porosimetry Without Using Mercury" Ceramic Engineering and Science Proceedings, 2002, p. 277–284.

Thelen, E. "Soil Permeability Tester", Franklin Institute Laboratories Notes: Franklin Inst. Journal, vol. 253, Apr. 1952, pp. 340–341.

"DWI—LB74 Porosity" http://www.dwi.twth–aachen.de/lb/74.html. Dec. 27, 1997.

Jena, Akshaya K. and Gupta, Krishna M. "A Novel Mercury Free Technique for Determination of Pore Volume, Pore Size and Liquid Permeability." P/M Science & Technology Briefs, vol. 4, No. 1, 2002. pp. 5–8.

Jena, Akshaya K. and Gupta, Krishna M. "Materials Pore–Sight Testing Pore Volume and Flow Through Porous Materials" Materials World, The Journal of the Institute of Materials, vol. 10, Num. 2, Feb. 2002.

Jena, Akshaya and Gupta, Krishna, "Measurement of Pore Volumen and Flow through Porous Materials", Material Testing; Jun. 2002.

* cited by examiner

METHOD AND APPARATUS FOR REDUCTION OF GAS BUBBLE FORMATION DUE TO GAS DIFFUSION THROUGH LIQUIDS CONTAINED IN PORES

BACKGROUND OF THE INVENTION

1. Field of the Invention

One application of the invention pertains to the field of porosimetry, or the measurement of the pore volume of substances. More particularly, the invention pertains to a method and apparatus for reducing bubble formation due to diffusion of gas through liquid.

2. Description of the Related Art

The prior art measures the pore volume of a sample in a liquid extrusion porosimeter using a weight and balance method. Specifically, as shown in FIG. 1, a sample (1) is wetted by a fluid and then placed above a membrane (2). A reservoir (8) of fluid (3) is located below the membrane (2). This fluid is the same type of fluid, which is used to wet the sample (1).

The sample (1) has larger pores (4) than the pores (5) of the membrane (2). Pressure (6) is applied, until liquid is forced out of the pores (4) in the sample, and into the reservoir (8) of fluid (3). The displaced fluid (7) flows out of the fluid reservoir (8) and is directed to a fluid displacement reservoir (9). The fluid displacement reservoir (9) is on a balance (10), which weighs the amount of the displaced fluid (7). A counterweight (11) on the balance (10) is used to determine the weight change due to the displaced fluid (7). This weight change is used in combination with calculations known in the art to determine the volume of the pores (4) in the sample (1).

The sealed system attempts to minimize air bubbles. However, the prior art preferably uses water or other high air diffusivity fluids. This increases the air bubbles in a sample, and potentially yields inaccurate results. Air bubbles also increase when the membrane (2) has small pores. The presence of air bubbles under the membrane (2) skews the measurement in the balance (10).

SUMMARY OF THE INVENTION

The apparatus of the present invention measures the porosity characteristics of a porous sample of material. The sample is preferably wetted, with the same type of fluid which is in the reservoir, prior to placing the sample on the wetted membrane in the porosimeter, or the fluid can be poured over the sample in the chamber. The wetting liquid spontaneously flows into the pores of the sample.

The porosimeter of the present invention comprises a source of pressure connected to a pressurizable chamber for holding the sample. The sample is supported by a membrane located between the sample and a fluid reservoir. The membrane has a plurality of pores with a size smaller than any of the sample pores, so that the bubble point pressure of the membrane is higher than the pressure needed to remove liquid from the pores of the sample. The reservoir and the membrane form a sealed chamber. The extruded fluid which passed from the pores of the sample through the pores of the membrane displaces the fluid in the fluid reservoir.

The fluid reservoir includes an inlet and an exit for fluid, such that in operation, as fluid enters the fluid reservoir through the membrane or the inlet, fluid already in the fluid reservoir is displaced through the exit. An inlet in the fluid displacement reservoir receives the fluid displaced from the fluid reservoir. A recirculation line receives fluid from the exit of the fluid displacement reservoir and circulates the fluid into the inlet of the fluid reservoir. The fluid moves through channels for efficient removal of gas bubbles. In a preferred embodiment, a pump is also included to recirculate the fluid. Fluid returned to the reservoir circulates over the bottom of the membrane, and sweeps air bubbles out of the reservoir. The removed air bubbles dissipate and do not affect the weight change measurements in the fluid displacement reservoir.

DETAILED DESCRIPTION OF THE INVENTION

Figure 1:
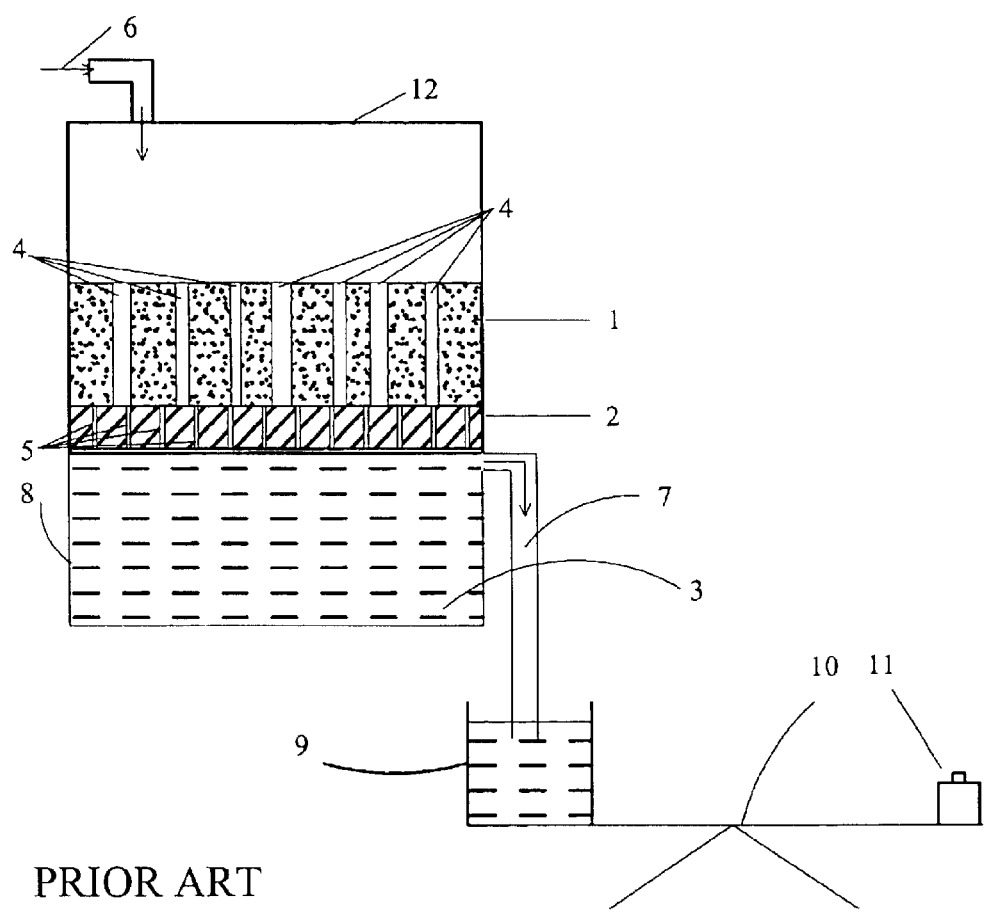
FIG. 1 shows a device for measuring pore volume as known in the prior art.
Figure 2:
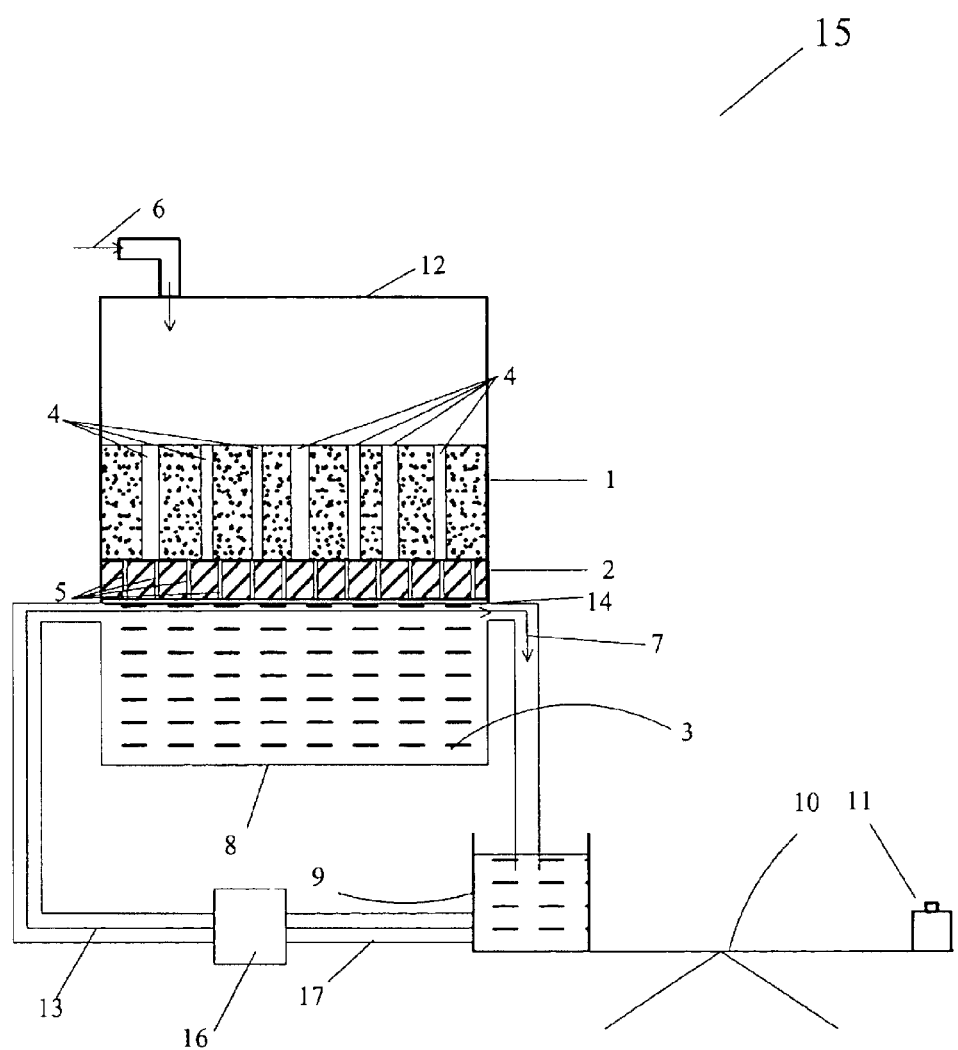
FIG. 2 shows a device for measuring pore volume in an embodiment of the present invention.

An example of a porosimeter (15) of the present invention is shown in FIG. 2. A sample (1) of a material whose porosity characteristics are to be determined, is located on a membrane (2).

The pores of the sample must be spontaneously filled with a wetting liquid with which the sample is to be tested preferably before the sample (1) is placed in the chamber (12) on the membrane (2). The same wetting liquid must be used to fill the pores of the membrane spontaneously. The testing begins when the sample and membrane pores (4) are filled with the wetting liquid.

The porosimeter (15) is especially useful in many applications when the fluid is water, or any high air diffusivity liquid. It is also useful when the membrane (2) has a small pore size. Both of these situations create a large number of air bubbles attached to the bottom of the membrane and skew weight measurements in the prior art systems.

The size of the pores (4) in the sample (1) may vary, depending on the nature of the sample. The membrane (2) needs to be chosen such that the smallest pore of interest in the sample is larger than the largest pore (5) in the membrane (2). The smallest pore of interest in the sample is such that all pores smaller than this pore have no significant influence on the application at hand. Therefore, the membrane (2) preferably has a very small pore size to accommodate many different samples (1). An example of a membrane which could be used is Poretics polycarbonate membrane, catalog No. 13705, from Osmonics, Inc, of Minnetonka, Minn.

The bubble point of a sample (1) is pressure at a point that can overcome the capillary action of the fluid within the largest pore (4). The size of the pores in a material determines the bubble point, or the pressure at which the liquid is extruded or forced out of the pores—the bubble point is inversely proportional to the size of the pores.

Since the sample (1) has a larger pore size than the membrane (2), the bubble point of the pores (4) in the sample (1) is lower than the bubble point of the pores (5) in the membrane (2). Therefore, when sufficient gas or air pressure (6) is applied to exceed the bubble point of the sample (1), the fluid is forced out of the relatively larger pores (4) in the sample (1), and passes through the relatively smaller pores (5) in the membrane (2). The amount of pressure (6) applied should be high enough to exceed the bubble point of the smallest of the sample pores (4) of interest, but below the bubble point of the membrane (2), so that eventually all of the fluid is forced out of the sample pores (4) of interest, but no fluid is forced out of the membrane pores (5).

A fluid reservoir (8) is located below the membrane (2). The reservoir (8) and the membrane (2) preferably form a seal to create a sealed system. The fluid (3) in the reservoir (8) is the same type of fluid as the fluid used to wet the sample (1). The extruded fluid which passed from the pores of the sample through the pores of the membrane displaces the fluid in the fluid reservoir (8). Thus, the total amount of fluid displaced from the reservoir will represent the amount of fluid which was trapped in the pores of the sample.

The displaced fluid (7) exits the reservoir (8) and is directed to a fluid displacement reservoir (9), which gathers the exited fluid. The fluid displacement reservoir (9) is preferably a covered beaker, but could be any container which effectively holds the fluid and minimizes evaporation. The fluid displacement reservoir (9) is preferably located on a balance (10).

Any air bubbles present on the bottom of the membrane (14) adversely affect the weight change in the fluid displacement reservoir (9) measured by the balance (10). Therefore, the present invention includes a recirculation line (17) to return the fluid (13) to the reservoir (8). In a preferred embodiment, a pump (16) recirculates the fluid (13) through the recirculation line (17). The pump (16) is preferably a peristaltic pump or any type of pump which does not introduce air bubbles into the system. The returned fluid (13) is preferably introduced at the opposite side of the reservoir to where the fluid exits with channels to sweep the air across the membrane.

The returned fluid sweeps the bubbles from the bottom of the membrane (14). These displaced bubbles exit the reservoir (8) and dissipate. This device is especially useful when the membrane (2) has small pores. Mechanical sweeping of the circulating fluid sweeps bubbles out of the reservoir (8) and the air bubbles dissipate. In addition, by pumping the same fluid back into the reservoir (8), the final weight change used for calculating pore volume is unaffected. Since air bubbles are not allowed to form, the weight change is continuously monitored. The pore volume is then calculated using the fluid weight measurement by techniques well known in the art.

Figure 3:
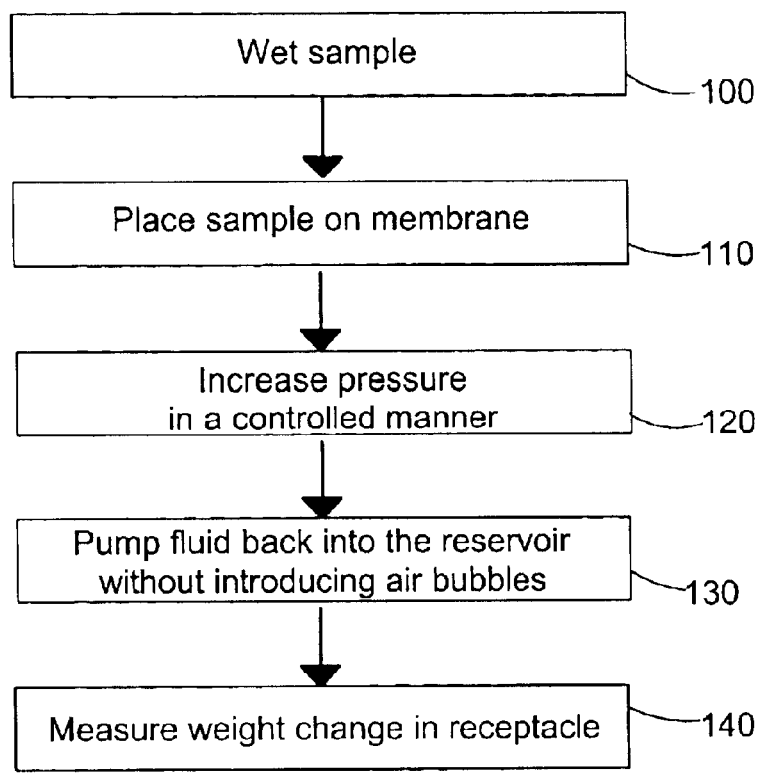
FIG. 3 shows a flowchart of one method of the present invention.

A flowchart of one method for measuring pore volume using the apparatus described above is shown in FIG. 3. First, the sample is wet in step (100), for example by a fluid such as water. At this point, the fluid has filled the pores (4) in the sample (1).

The sample is placed on the membrane (2) whose pores are also filled with the wetting liquid in step (110). The pores (5) in the membrane (2) have a smaller pore size than any of the pores (4) in the sample (1).

The pressure is increased in a controlled manner, preferably in small steps of a few hundredths of a psi, in step (120). Once the pressure exceeds the bubble point pressure, the fluid in the pores (4) begins to be pushed out of the largest pores (4) in the sample (1). The extruded fluid enters the fluid reservoir (3), causing the fluid level in the reservoir (8) to rise. Consequently, some of the fluid (7) exits the reservoir (8), and is directed into the fluid displacement reservoir (9).

The pressure (6) is continually increased, preferably in small steps, and maintained until the fluid in the fluid displacement reservoir (9) reaches equilibrium. Equilibrium is reached when the fluid level is no longer increasing.

The fluid entering the balance is recirculated back into the reservoir in step (130). Although this step is shown using a pump (16) and a recirculation line (17) in the figures, any device which returns the fluid from the fluid displacement reservoir (9) to the fluid reservoir (8) without introducing air bubbles is within the spirit of the present invention.

This step is preferably accomplished using a pump (16) and a recirculation line (17). This step preferably occurs simultaneously with step (120). The fluid is preferably introduced back into the reservoir (8) at the opposite side of the reservoir (8) to where the fluid flows out.

The circulating fluid returned to the reservoir (8) sweeps the bubbles from the bottom of the membrane (2). The sweeping motion dislodges bubbles from under the membrane (2). The dislodged bubbles exit the reservoir (8) and dissipate. This mechanical sweeping of circulating fluid sweeps the bubbles out of the reservoir (8), thereby reducing the air bubbles in the liquid.

Once the fluid in the fluid displacement reservoir (9) reaches equilibrium, the weight change in the fluid displacement reservoir (9) is measured in step (140). The pore volume is then calculated using the weight change measurement by techniques well known in the art.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A method of evaluating the porosity characteristics of a sample of material having a plurality of pores using a porosimeter comprising a pressurizable sample chamber for holding the sample, a membrane located at a bottom of the sample chamber and having a plurality of pores, wherein the membrane pores have a size smaller than any of the sample pores of interest, a fluid reservoir located below the membrane, and a fluid displacement reservoir, comprising the steps of:

a) placing the sample in the sample chamber, on the membrane;

b) wetting the sample with a fluid until the fluid has entered substantially all of the pores in the sample and the membrane;

c) applying a pressure in the sample chamber which is greater than a bubble point pressure of the sample, but less than a bubble point pressure of the membrane, such that as fluid enters the fluid reservoir through the membrane, it displaces fluid already in the fluid reservoir into the fluid displacement reservoir;

d) pumping the displaced fluid back into the fluid reservoir along a bottom of the membrane such that air bubbles stuck to the membrane are swept away from the membrane; and e) measuring a weight change in the fluid displacement reservoir after a weight in the fluid displacement reservoir reaches an equilibrium.

2. The method of claim 1, wherein the fluid is a fluid with high air diffusivity.

3. The method of claim 2, wherein the fluid is water.

4. The method of claim 1, further comprising the step of calculating a pore volume of the sample using the fluid weight change measured in step (e).

5. The method of claim 1, wherein the pump is a peristaltic pump.

6. The method of claim 1 in which the step of wetting the sample further comprises applying pressure at greater than the bubble point of the sample to force fluid into the pores of the sample.

7. An improved method of evaluating the porosity characteristics of a sample of material having a plurality of pores, using a porosimeter comprising a pressurizable sample chamber for holding the sample, a membrane located at a bottom of the sample chamber and having a plurality of pores, wherein the membrane pores have a size smaller than any of the sample pores of interest, a fluid reservoir located below the membrane, and a fluid displacement reservoir, wherein a wetted sample is subjected to a pressure in the sample chamber which is greater than a bubble point pressure of the sample, but less than a bubble point pressure of the membrane, such that as fluid enters the fluid reservoir through the membrane, it displaces fluid already in the fluid reservoir into the fluid displacement reservoir, wherein the improvement comprises:

recirculating the displaced fluid through the fluid reservoir along the membrane such that air bubbles stuck to the membrane are swept away from the membrane.

8. The method of claim 7, wherein the fluid is a fluid with high air diffusivity.

9. The method of claim 8, wherein the fluid is water.

10. The method of claim 7, further comprising the step of calculating a pore volume of the sample using the fluid weight change in the fluid displacement reservoir.

11. The method of claim 7, wherein the pump is a peristaltic pump.

12. A porosimeter for evaluating the porosity characteristics of a sample of material having a plurality of pores comprising:

a) a pressurizable sample chamber for holding the sample, comprising a membrane located at a bottom of the sample chamber and having a plurality of pores, wherein the membrane pores have a size smaller than any of the sample pores;

b) a fluid reservoir located below the membrane, comprising an inlet and an exit for fluid, such that as fluid enters the fluid reservoir through the membrane or the inlet, it displaces fluid already in the fluid reservoir through the exit;

c) a fluid displacement reservoir comprising an inlet and an exit, wherein the inlet receives the fluid displaced from the fluid reservoir; and d) a recirculation line that receives fluid from the exit of the fluid displacement reservoir and circulates the fluid through the inlet of the fluid reservoir and along the membrane such that air bubbles stuck to the membrane are swept away from the membrane.

13. The porosimeter of claim 12, further comprising a balance for measuring weight change of the fluid displacement reservoir continuously as the fluid moves continuously through the displacement reservoir.

14. The porosimeter of claim 12, further comprising a fluid having high air diffusivity.

15. The porosimeter of claim 14, wherein the fluid is water.

16. The porosimeter of claim 12, wherein the porosity characteristic being evaluated is the pore volume of the sample.

17. The porosimeter of claim 12, further comprising a pump connected to the recirculation line, wherein the pump aids in circulation of the fluid.

18. The porosimeter of claim 17, wherein the pump is a peristaltic pump.

19. An improved porosimeter for evaluating the porosity characteristics of a sample of material having a plurality of pores of the type comprising a pressurizable sample chamber for holding the sample, a membrane located at a bottom of the sample chamber and having a plurality of pores, wherein the membrane pores have a size smaller than any of the sample pores of interest, wherein the improvement comprises:

a) a fluid reservoir located below the membrane, comprising an inlet and an exit for fluid, such that as fluid enters the fluid reservoir through the membrane or the inlet, it displaces fluid already in the fluid reservoir;

b) a fluid displacement reservoir comprising an inlet and an exit, wherein the inlet receives the fluid displaced from the fluid reservoir; and c) a recirculation line that receives fluid from the exit of the fluid displacement reservoir and circulates the fluid through the inlet of the fluid reservoir and along the membrane such that air bubbles stuck to the membrane are swept away from the membrane.

20. The porosimeter of claim 19, further comprising a balance for measuring weight change of the fluid displacement reservoir after a weight in the fluid displacement reservoir reaches an equilibrium.

21. The porosimeter of claim 19, further comprising a fluid having high air diffusivity.

22. The porosimeter of claim 21, wherein the fluid is water.

23. The porosimeter of claim 19, wherein the porosity characteristic being evaluated is the pore volume of the sample.

24. The porosimeter of claim 19, further comprising a pump connected to the recirculation line, wherein the pump aids in circulation of the fluid.

25. The porosimeter of claim 24, wherein the pump is a peristaltic pump.

* * * * *